United States Patent [19]

Gaffar

[11] 4,138,477

[45] Feb. 6, 1979

[54] COMPOSITION TO CONTROL MOUTH ODOR

[75] Inventor: Maria Corazon S. Gaffar, Somerset, N.J.

[73] Assignee: Colgate Palmolive Company, New York, N.Y.

[21] Appl. No.: 691,262

[22] Filed: May 28, 1976

[51] Int. Cl.$^2$ .................... A61K 7/16; A61K 7/18; A61K 9/68; A61K 31/315

[52] U.S. Cl. .................. 424/52; 424/48; 424/49; 424/56; 424/78; 424/81; 424/83; 424/145; 424/289

[58] Field of Search ................. 424/48–58, 424/78–83, 145, 289

[56] References Cited

U.S. PATENT DOCUMENTS

| | | | |
|---|---|---|---|
| 1,593,485 | 7/1926 | Crosnier | 424/76 |
| 3,070,510 | 12/1962 | Cooley | 424/52 |
| 3,429,963 | 2/1969 | Shedlovsky et al. | 424/56 |
| 3,943,267 | 3/1976 | Randol | 424/49 |
| 3,956,480 | 5/1976 | Dichter | 424/49 |
| 4,022,880 | 5/1977 | Vinson | 424/49 |

OTHER PUBLICATIONS

Websters Third New International Dictionary (unabridged) 1963, p. 2174, "Sorbic Acid and/or Sorbate."
Crisp et al., "Zinc Polycarboxylate Cements:" J. Dent res. 1976, 55, 2, pp. 299–308.
Begala et al., J. of Physical Chem., (1972), 76, 2, pp. 254–260.

*Primary Examiner*—Shep K. Rose
*Attorney, Agent, or Firm*—Robert L. Stone; Murray M. Grill; Herbert S. Sylvester

[57] ABSTRACT

A novel composition to prevent and control mouth odor, which is also effective in preventing calculus, plaque, caries and periodontal disease containing as the essential agent, a zinc-polymer combination formed by the reaction or interaction of a zinc compound with an anionic polymer containing carboxylic, sulfonic and/or phosphonic acid radicals.

10 Claims, No Drawings

COMPOSITION TO CONTROL MOUTH ODOR

This invention relates to novel oral formulations comprising a combination of a zinc compound and an anionic polymer as an effective agent against mouth odor, plaque, calculus and periodontal disease.

The prior art is replete with oral compositions containing zinc salts such as zinc chloride, zinc iodide, zinc fluoride, zinc sulfide, zinc phenol sulfonate and the like as antiseptic agents, and correctives of oral conditions such as pyorrhea. Zinc chloride has commonly been used in oral formulations for its astringency properties. Zinc phenol sulfonate has been utilized in the prior art dentifrice compositions as an anti-plaque and anti-calculus agent as well as an odor inhibitor of fermentation and putrefaction which occurs in the oral cavity. These soluble zinc salts have the dual disadvantage of leaving an unpleasant astringent taste in the mouth as well as having short-lived efficacy against plaque, calculus and as an odor inhibitor.

Sparingly soluble zinc salts such as zinc citrate, zinc $C_{14}$-alkyl maleate, zinc benzoate, zinc caproate, zinc carbonate, zinc citrate, etc. have been used in dentifrice formulations to prolong the anti-calculus and anti-plaque effectiveness of the zinc ions due to the slow dissolution of the zinc salts in the saliva. The sparingly soluble characteristic of these zinc salts promotes longevity of action against plaque and calculus at the expense of initial or immediate efficacy.

The use of a zinc complex of a specific diketone as an agent for combating tartar and tooth discoloration is also known, as set forth in German Patent No. 2,229,466. Thus, it is apparent that zinc compounds generally are known to have deodorizing properties as well as efficacy against plaque, calculus and possibly periodontal disease.

Also known is the use of a water soluble sodium salt of a linear anionic polymer as an anti-calculus agent, as set forth in U.S. Pat. No. 3,429,963 to Shedlovsky. This patent discloses that the hydrolyzed copolymers and/or polymers prevent the deposition of calculus by means of their calcium sequestration properties. However, there is no suggestion in this patent, nor in any of the known prior art, that a combination of a zinc salt and an anionic polymer is unusually effective in preventing and controlling mouth odor while simultaneously preventing calculus, plaque, caries and periodontal disease.

Accordingly, it is an object of this invention to provide an oral composition containing as the mouth odor inhibitor, the reaction product of a zinc salt with an anionic polymer.

Another object of instant invention is to provide an oral composition effective in inhibiting mouth odor over a protracted period of time.

Still another object of this invention is to provide an oral composition effective in inhibiting plaque, calculus, caries and periodontal disease.

It has been found, through radioisotope studies, that anionic polymers can be adsorbed onto oral surfaces. Accordingly, an effective method of controlling mouth odor entails the use of an oral composition comprising a zinc polymer salt or complex formed by combining zinc compounds with anionic polymers. The positively charged zinc ions can react with the polymeric carboxyl, sulfonic or phosphonic acid groups of the anionic polymers to form zinc-polymer combinations. In the presence of excess acidic groups, the zinc-polymer combinations adsorb onto the oral surfaces such as the teeth and oral mucosa, thereby forming a reservoir of zinc ions capable of being gradually released with time into the oral environment.

Accordingly, it has now been found that mouth odor can be controlled by treating the oral cavity with a combination of a zinc compound and an anionic polymer. Said zinc-polymer combinations provide both a means of attachment to the oral cavity as well as form a reservoir of zinc ions which are gradually released over a protracted period of time as an effective means to combat mouth odor, plaque, calculus, and periodontal disease. In addition, the zinc-polymer combinations decrease the high astringency which is characteristic of zinc ions, thereby leaving a more pleasant taste in the mouth.

It has been ascertained through equilibrium dialysis studies against water that the zinc ions are bound to the anionic polymer and are slowly released with time as clearly indicated by the results in Table I, wherein 0.025% zinc oxide plus 2% of a copolymer of vinyl methyl ether and maleic anhydride having a molecular weight of 250,000 (Gantrez 119) was tested against zinc oxide per se.

Table I

| | Equilibrium Dialysis Studies | | |
|---|---|---|---|
| | Rate of Dissociation | | |
| Compound | 10 Min | 1 Hr | 24 Hrs |
| $Zn^{+2}$ + Gantrez 119* | 0 | 0 | 53 |
| $Zn^{+2}$ + $H_2O$** | 21 | 70 | 100 |

*0.025% zinc oxide + 2% Gantrez 119; pH adjusted to 6.5 with 3N $NH_4OH$
**0.025% zinc oxide + 1N HCl; pH adjusted to 6.5 with 3N $NH_4OH$ The above table clearly shows that no zinc was detected in the dialysate (outside membrane) after 10 minutes, and after 1 hour of dialysis; and only 53% zinc was found in the dialysate after 24 hours dialysis. Whereas, in the absence of the polymer, 21% zinc was detected in the dialysate after only 10 minutes, 70% zinc was found after only 1 hour and 100% zinc was found in the dialysate after 24 hours dialysis. In the presence of saliva salts, the zinc ions are bound to the polymer and are even more gradually released with time, with only 7% zinc being detected in the dialysate after 24 hours. In contrast, in the absence of the polymer, the zinc is dialyzed out 7% after 10 minutes; 50% after 1 hour; and 100% after 24 hours.

The anionic polymers are well known in the art. Preferably, the polymer is one which is linear and water-soluble. For example, it may be soluble in water, when in its sodium or ammonium salt form, at least to the extent of the concentration in which it is employed (0.1% to 10%). See for instance the anionic polymeric materials described in U.S. Pat. Nos. 2,984,639, 3,325,402, 3,429,963, the article on "Polyelectrolytes" in Vol. 10 of Encyclopedia of Polymer Science pages 781 ff, particularly pages 781, 782 and 784 listing various polyelectrolytes. The anionic polymers employed herein preferably contain ionizable carboxyl, sulfonic or phosphonic groups. A preferred type of polymers has its ionic substituents on a polymer chain which is hydrocarbon preferably aliphatic hydrocarbon (e.g. a vinyl polymer). Typical of such anionic polymers are copolymers of an unsaturated polybasic carboxylic acid or anhydride thereof (preferably dibasic and having 4 carbon atoms per molecule) and of an olefin having 2 or more carbon atoms per molecule; polyolefin sulfonates; polyolefin phosphonates; and polyolefin phosphates, the olefin group containing 2 or more carbon atoms. Suitable examples include:

1. A copolymer of maleic anhydride with ethylene, or styrene, or isobutylene, or polymethyl vinyl ether, or polyethylvinyl ether, having recurring groups:

wherein M and $M_1$ are individually hydrogen, sodium, potassium or ammonium and may be the same or different, and X is ethylene, styrene, isobutylene, methylvinyl ether, and ethylvinyl ether.

2. A polyacrylic acid and polyacrylates thereof having recurring groups:

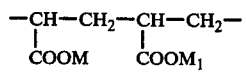

wherein M and $M_1$ have the same meaning as above.

3. A polyitaconic acid and polyitaconates thereof having recurring groups:

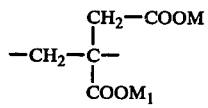

wherein M and $M_1$ have the same meaning as above.

4. A polyolefin sulfonate having recurring groups:

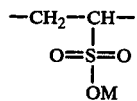

wherein M has the same meaning as above.

5. A polyvinyl phosphonate having recurring groups:

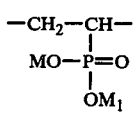

wherein M and $M_1$ have the same meaning as above.

6. A polyvinyl phosphate having recurring groups:

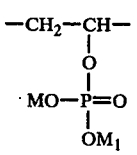

Good results have been obtained with anionic polymers of very high molecular weight such as about 500,000 or 1,000,000 as well as of relatively low molecular weights of at least 1,000 and preferably 1,500 to 500,000. The anionic polymer constitutes about 0.1 to 10% by weight and preferably 0.5–1.5% of the oral composition.

The zinc compounds that form the zinc-polymer combination by reaction or interaction with said anionic polymer may be any physiologically acceptable zinc salt including the water soluble and insoluble, organic and inorganic zinc salts. Any zinc compound equivalent to 1.5 mg/ml zinc may be mixed with the anionic polymer. Examples of suitable zinc compounds that may be employed include:

| | |
|---|---|
| zinc acetate | zinc isovalerate |
| zinc acetylacetonate | zinc D-lactate |
| zinc ammonium sulfate | zinc DL-lactate |
| zinc benzoate | zinc laurate |
| zinc bromide | zinc hexafluorosilicate |
| zinc beryllium orthosilicate | zinc methacrylate |
| zinc borate | zinc molybdate |
| zinc butylphthalate | zinc naphthenate |
| zinc butylxanthate | zinc octoate |
| zinc caprylate | zinc oleate |
| zinc carbonate | zinc orthophosphate |
| zinc chloroanilate | zinc phenolsulfonate |
| zinc chlorate | zinc pyridine-2-thiol-1-oxide |
| zinc chromate | zinc pyrophosphate |
| zinc citrate | zinc resinate |
| zinc cyclohexanebutyrate | zinc salicylate |
| zinc chloride | zinc sulfate |
| zinc gallate | zinc nitrate |
| zinc fluoride | zinc selenide |
| zinc alpha-glucoheptonate | zinc stearate |
| zinc gluconate | zinc sulfanilate |
| zinc glycerophosphate | zinc tartrate |
| zinc hydroxide | zinc tellurate |
| zinc 8-hydroxyquinoline | zinc tungstate |
| zinc 12-hydroxystearate | zinc valerate |
| zinc iodide | zinc vanadate |
| zinc acrylate | zinc tribromosalicylanilide |
| zinc oxide | zinc ricinoleate |
| zinc propionate | |

Although the majority of the zinc salts might have limited solubility in water, the presence of the anionic polymer does increase the solubility of the combination. Zinc oxide or zinc propionate, for example, are insoluble in water but in the presence of adequate amounts of the anionic polymer they are solubilized. The pH thereof can be adjusted to 5.5 to 7.0 with dilute $NH_4OH$ and the clarity of the solutions are retained. Many insoluble zinc salts are rendered soluble when combined with the anionic polymers, thereby providing a means of following the interaction or reaction between zinc and the anionic polymer. The zinc compound constitutes about 0.01–5% and preferably 0.025–1% by weight of the oral composition.

The solubility of the zinc-polymer combination appears to be a factor in the activity against odor formation. Soluble combinations of anionic polymer and zinc salt are very effective in inhibiting odor formation, whereas insoluble zinc-polymer combinations are less effective in reducing odor formation. Soluble combinations of the anionic polymer with zinc oxide, or zinc propionate are very effective in inhibiting VSC (volatile sulfur compounds), whereas the insoluble zinc-polymer combinations such as polymer + zinc pyrophosphate, zinc glycerophosphate, or zinc, 8-OH quinoline were ineffective or only slightly effective.

Another factor which influences the efficacy of the zinc-polymer combination as an odor-inhibitor is the counterion in the original zinc compound. The zinc glyconate, and zinc alpha-glucoheptonate polymer combinations are soluble but substantially inactive in reducing mouth odor. The zinc salicylate-polymer combinations are possibly effective against periodontal disease because of the anti-inflammatory properties of the salicylate counterion in addition to the benefit from the zinc ions of the suppression of mouth odor.

Aqueous solutions and dispersions of various zinc compounds were tested in an in vitro system consisting of whole human saliva. L-cysteine as substrate, and incubated for 3 hours at 37° C. in an airtight container. After incubation, the headspace VSC (volatile sulfur compounds) formation was measured by an instrumental GC-flame photometric technique. Since mouth odor has been attributed to the presence of volatile sulfur compounds such as hydrogen sulfide, methyl mercaptan and dimethyl sulfide resulting from putrefactive processes occuring in the oral cavity, aforesaid in vitro test provide results comparable to in vivo sensory evaluations. The results, as set forth in Table II, show excellent VSC inhibition for the zinc oxide, zinc chloride and zinc propionate combinations with the anionic polymer. Zinc chloride plus water was used as the control compound.

Table II

| Compound* | Volatile Sulfur % VSC Inhibition |
|---|---|
| Zinc oxide + G-119[1] (soluble) | 52 |
| Zinc chloride + G-119 (soluble) | 36 |
| Zinc propionate + G-119 (soluble) | 53 |
| Zinc gluconate + G-119 (soluble) | 15 |
| Zinc alpha-glucoheptonate + G-119 (soluble) | 15 |
| Zinc pyrophosphate (insoluble) | 12 |
| Zinc glycerophosphate + G-119 (slightly soluble) | 13 |
| Zinc 8-OH quinoline + G-119 (slightly soluble) | 24 |
| Zinc salicylate + G-119 (soluble) | 17 |
| Zinc chloride + H$_2$O | 54 |

*Zinc equivalent to 1.6 mg/ml; G-119 = 0.1%; pH between 6.5 to 7.0
[1]G-119 is the anionic polymer defined in Table I
indicative of promotion of odor formation as opposed to inhibition In addition to the efficacy of the zinc-polymer combinations as a mouth odor inhibitor, the taste thereof is distinctly different from, and an improvement over, that of zinc chloride as evidenced by a testing program wherein a panel of five persons tasted two samples, via a mouthrinse, containing equivalent concentrations of zinc ions; one sample containing zinc chloride/polymer combination and the other containing zinc chloride/water plus 0.2% flavor (both at a pH between 5.5–5.8). The participants agreed, without exception, that the two samples were distinctly different and that the zinc chloride-polymer sample had very little of the astringent, metallic taste characteristic of zinc ions. These results show that the presence of the polymer improves the taste of zinc-containing solutions by eliminating the astringent taste and the numbing of the tongue attributable to the zinc ions. Thus, it is apparent that the zinc-polymer combinations are particularly useful in formulations where the taste of zinc creates a disadvantage.

Aqueous dispersions or solutions of zinc-polymer combination may be produced by adding a zinc salt in the form of a dilute solution, a paste or in the dry state, to a dilute solution of anionic polymer, and stopping the addition before the amount of zinc salt is such as to form a precipitate or gel. With good agitation and careful addition not to exceed the amount of maximum solubility of the zinc-polymer complex, a clear solution or dispersion is obtained. This phenomena is clearly indicated in Example 2. The anionic polymer solution is preferable adjusted to a pH of about 5.5 with ammonium hydroxide or other suitable base prior to the addition of the zinc salt. The pH of the final zinc polymer salt solution is about 4.5–6.0. For example, a suitable zinc polymer salt or complex is formed by adding 0.050M of a zinc salt to 500 ml of a 2% solution of a copolymer of methylvinyl ether and maleic anhydride, (adjusted to a pH of 5.5 and 3N ammonium hydroxide) and mixing well. The final solution or dispersion of the zinc-anionic polymer complex preferably has a pH of about 4.5–6.0. It is believed that the ionized carboxyl groups react or interact with the zinc ion to form a zinc-polymer salt or complex. See the article by Crisp et al, J Dent Res March–April 1976, 55, 2, pp.299–308, particularly pp.305–307; and by Begala et al, The Journal of Physical Chemistry (1972), 76, 2, pp.254–260 dealing with counterion binding by polycarboxylates. The experimental evidence shows that the binding of zinc to polymers is mostly ionic. Ionic binding leads to either:

a) chain bridging salts:

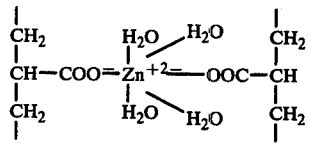

b) intra chain salts:

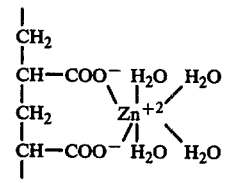

c) pendant half salts:

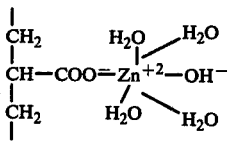

d) chelate (ring) structure with copolymers of vinylmethyl ether and maleic anhydride, since divalent cations like zinc form a chelate with the ether oxygen and one carboxyl group:

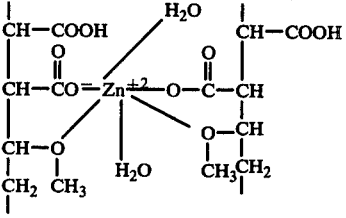

-or-

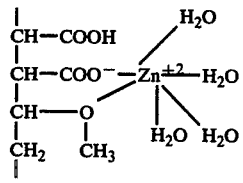

Accordingly, it is believed that the zinc-polymer complex is ionically bound, but the exact type of binding (which may also exist as a mixture of above structures) has not been ascertained.

The following examples are given to illustrate this invention further. In this application all proportions are by weight unless otherwise indicated.

EXAMPLE 1

0.2gm zinc chloride is dissolved in 15 ml water and added to a 4% aqueous solution of the copolymer of maleic anhydride and methylvinyl ether with agitation and subsequently diluted to 200ml. A clear solution of the zinc-polymer complex is obtained.

EXAMPLE 2

(a) 100g of an aqueous zinc oxide paste containing 0.5% zinc is prepared and added slowly with continuous stirring to 25 ml of a 1% aqueous solution of methylvinyl ether-maleic anhydride copolymer and subsequently diluted with 75 ml water. The final solution has a pH of 5.5 and is slightly cloudy. The ratio of zinc to anionic polymer is 1:2.

(b) 100 gm of an aqueous zinc oxide paste containing 0.25% zinc is added to 100gm of an aqueous solution containing 0.25% methylvinyl ether-maleic anhydride copolymer with continuous agitation. The final solution has a pH of 6.5 and is turbid. The ratio of zinc to anionic polymer is 1:1.

(c) A final solution of zinc-polymer complex is prepared as above containing 0.25% zinc and 1.0% anionic polymer, a ratio of 1:4, which has a pH of 3.5 and is clear. With the addition of about 10ml. 3N ammonium hydroxide to said clear solution, the pH is adjusted to 6.8 (pH in the oral cavity) and the solution retains its clarity.

This example clearly shows that the ratio of zinc salt to anionic polymer is dependant on the solubility of the final zinc-polymer complex formed, maximum solubility being evidenced by a clear solution which is preferable although a slight cloudiness is also acceptable.

EXAMPLE 3

A zinc-polymer complex is prepared by mixing 50ml. of 0.05M aqueous solution of the following zinc salts with 50ml of a 2% aqueuous solution of methylvinyl ether-maleic anhydride copolymer and the pH is adjusted to 5-6 with ammonium hydroxide. The ratio of zinc to polymer is 1:4.

a. zinc oxide which contains 80.34% zinc and is water insoluble.
b. zinc chloride which contains 47.97% zinc and is water soluble.
c. zinc glycerophosphate which contains 27.77% zinc and is soluble in water and insoluble in alcohol.
d. zinc salicylate which contains 19.25% zinc and is soluble in water and alcohol.
e. zinc alpha glucoheptonate which contains 19.7% zinc and is water soluble.
f. zinc propionate which contains 30.91% zinc and is only 32% soluble in water and 28% soluble in alcohol.
g. zinc salt of 8-hydroxyquinoline which contains 18.48% zinc and is water insoluble.
h. zinc gluconate which contains 25% zinc and is water soluble.
i. zinc pyrophosphate which contains 42.91% zinc and is insoluble in water, but soluble in dilute mineral acids.

The final solutions containing the zinc-anionic polymer complex were all clear except for the solutions containing zinc pyrophosphate which was cloudy and turbid, the zinc 8-hydroxyquinoline which was yellow and turbid and the zinc glycerophosphate which was cloudy and slightly turbid. The zinc propionate which was initially a cloudy precipitate became clear upon the addition of the anionic polymer.

While particularly good results in terms of odor inhibition and other salutary effects in the oral cavity and on tooth surfaces, have thus far been obtained by applying simply the aqueous solutions or dispersions of the zinc-polymer complex, it will be understood that it is within the broader aspect of the invention to incorporate said complex into oral compositions generally, such as clear or cloudy mouth rinses and transparent or opaque toothpastes, troches, chewing gum, tablet or powder containing a dental vehicle. Likewise, the complex may be formed in situ, during the preparation of said oral compositions or even on dilution in the mouth; or the zinc compound and the anionic polymer may merely act cooperatively within said oral cavity and not form a detectable complex.

The vehicle, often referred to as a dental vehicle contains liquids and solids. In general, the liquid comprises water and/or a humectant such as glycerine, sorbitol, propylene glycol or polyethylene glycol 400 including suitable mixtures thereof. It is usually advantageous to use a mixture of both water and one or two humectants. The total liquid content is generally about 20–90 percent by weight of the vehicle. In transparent and translucent vehicles, the liquid content of the toothpaste may be about 20–90 percent by weight, while in opaque vehicles the total liquid content is usually about 20–50 percent by weight. The preferred humectants are glycerine and sorbitol. Typically clear, that is transparent or translucent, vehicle contains 0–80 percent by weight of glycerine, about 20–80 percent by weight of sorbitol and about 20–80 percent by weight of water. Opaque vehicles typically contain about 15–35 percent by weight of glycerine and about 10–30 percent by weight of water.

The solid portion of the vehicle is a gelling agent. In the instant invention the gelling agent includes alkali metal carboxymethyl cellulose in amount of at least about 0.25 percent by weight of the vehicle. Additional gelling agents may also be present. Gelling agents which may be additionally present include viscarin, gelatin, starch, glucose, sucrose, polyvinyl pyrollidone, polyvinyl alcohol, gum tragacanth, gum karaya, hydroxy propyl cellulose, methyl cellulose, carboxyethyl cellulose, sodium alginate, Laponite CP or SP, which are each synthetic inorganic complex silicate clays sold under trademark by Laporte Industries, Ltd., and magnesium aluminum silicate gel. The solid portion or gelling agent of the vehicle is typically present in amount of about 0.25–10 percent by weight of the toothpaste and preferably about 0.5–8 percent by weight. Alkali metal carboxymethyl cellulose includes the lithium, sodium and potassium salts.

Any suitable substantially water-insoluble polishing agent may be added to the gel vehicle. There is a relatively large number of such materials known in the art. Representative materials include, for example, dicalcium phosphate, tricalcium phosphate, insoluble sodium metaphosphate, aluminum hydroxide, magnesium carbonate, calcium carbonate, calcium pyrophosphate, calcium sulfate, bentonite, etc., including suitable mixtures thereof. It is preferred to use the water-insoluble phosphate sodium metaphosphate and/or a calcium phosphate, such as dicalcium phosphate dihydrate. In general, these polishing agents will comprise a major proportion by weight of the solid ingredients. The polishing agent content is variable, but will generally be up to about 75 percent by weight of the total composition, generally about 20–75 percent; although, as indicated below, even lower amounts of polishing agent can be employed.

Any suitable surface-active or detersive material may be incorporated in the gel vehicle. Such compatible materials are desirable to provide additional detersive, foaming and antibacterial properties depending upon the specific type of surface-active material and are selected similarly. These detergents are water-soluble organic compounds usually, and may be anionic, non-ionic, or cationic in structure. It is preferred to use the water-soluble non-soap or synthetic organic detergents, usually. Suitable detersive materials are known and include, for example, the water-soluble salts of higher fatty acid monoglyceride monosulfate detergent (e.c., sodium coconut fatty acid monoglyceride monosulfate), higher alkyl sulfates (e.g., sodium lauryl sulfate), alkyl aryl sulfonate (e.g., sodium dodecyl benzene sulfonate), higher fatty acid esters of 1,2-dihydroxypropanesulfonate) and the like.

The various surface-active materials may be used in any suitable amount, generally from about 0.05 to about 10 percent by weight, and preferably from about 0.5 to 5 percent by weight of the dentifrice composition.

It is a further embodiment of the present invention to use the substantially saturated higher aliphatic acyl amides of lower aliphatic amino carboxylic acid compounds, such as those having 12 to 16 carbons in the acyl radical, and as more particularly described in U.S. Pat. No. 2,689,170 issued Sept. 14, 1954. The amino acid portion is derived generally from the lower aliphatic saturated monoamino carboxylic acids having about 2 to 6 carbons, usually the monocarboxylic acid compounds. Suitable compounds are the fatty acid amides of glycine, sarcosine, alanine, 3-aminopropanoic acid and valine having about 12 to 16 carbons in the acyl group. It is preferred to use the N-lauroyl myristoyl and palmitoyl sarcoside compounds, however, for optimum effects.

The amide compounds may be employed in the form of the free acid or preferably as the water-soluble salts thereof, such as the alkali metal, ammonium, amine and alkylolamine salts. Specific examples thereof are sodium and potassium N-lauroyl, myristoyl and palmitoyl sarcosides, ammonium and ethanolamine, N-lauroyl sarcoside, N-lauroyl sarcosine, and sodium N-lauroyl glycine and alanine. For convenience herein, reference to "amino carboxylic acid compound," "sarcoside," and the like refers to such compounds having a free carboxylic group or the water-soluble carboxylate salts.

Various other materials may be incorporated in the vehicles of this invention. Examples thereof are preservatives, silicones, chlorophyll compounds, ammoniated materials such as urea, diammonium phosphate and mixtures thereof, materials which can increase contrast with the particles, such as titanium dioxide and other constituents. These adjuvants are incorporated in the instant compositions in amounts which do not substantially adversely affect the properties and characteristics suitably selected and used in proper amount depending upon the particular type of preparation involved.

Antibacterial agents may also be employed in the gelled vehicles of the instant invention. Typical antibacterial agents include:

$N^1$-(4-chlorobenzyl)-$N^5$-(2,4-dichlorobenzyl) biguanide;
p-chlorophenyl biguanide;
4-chlorobenzhydryl biguanide;
4-chlorobenzhydrylguanylurea;
N-3-lauroxypropyl-N-p-chlorobenzylbiguanide;
1,6-di-p-chlorophenylbiguanide hexane;
1-(lauryldimethylammonium)-8-(p-chlorobenzyldimethylammonium) octane dichloride;
5,6-dichloro-2-guanidinobenzimidazole;
$N^1$-p-chlorophenyl-$N^5$-laurylbiguanide;
5-amino-1,3-bis(2-ethylhexyl)-3-methylhexahydro pyrimidine; and their non-toxic acid addition salts.

The antibacterial agent, when present, is employed in amounts of about 0.1–5 percent by weight, preferably about 0.05–5 percent.

Any suitable flavoring or sweetening materials may be employed in formulating a flavor for the compositions of the present invention. Examples of suitable flavoring constituents include the flavoring oils, etc., oils of spearmint, peppermint, wintergreen, sassafras, clove, sage, eucalyptus, marjoram, cinnamon, lemon and orange, as well as sodium methylsalicylate. Suitable sweetening agents include sucrose, lactose, maltose, sorbitol, sodium cyclamate and saccharine. Suitably, flavor and sweetening agent may together comprise from about 0.01 to 5 percent or more of the compositions of the instant invention.

A fluorine-containing compound having a beneficial effect on the care and hygiene of the oral cavity, e.g., diminution of enamel solubility in acid and protection of the teeth against decay may also be incorporated in the gelled vehicle. Examples thereof include sodium fluoride, stannous fluoride, potassium fluoride, potassium stannous fluoride ($SnF_2$-KF), sodium hexafluorostannate, stannous chlorofluoride, sodium fluorozirconate, and sodium monofluorophosphate. These materials, which disassociate or release fluorine-containing ions in water, suitably may be present in an effective but non-toxic amount, usually within the range of about 0.01 to 1 percent by weight of the water-soluble fluorine content thereof.

The oral preparation may also be a liquid such as mouth rinse which typically contains 20–99% by weight of an aqueous lower aliphatic alcohol, preferably having about 1–30% by weight alcohol such as ethanol, n-propyl, or isopropyl alcohol.

Such oral preparations are typically applied by brushing the teeth or rinsing the oral cavity for 30–90 seconds at least once daily. Typical oral preparations of the invention which can be applied in this manner are set forth below.

EXAMPLE 4

| Preparation of Zinc-Polymer Mouthrinse Total volume = 1 liter | | |
|---|---|---|
| Solution A (Mouthrinse concentrate) | % (gms/100 ml) | On mixing with B Final conc: % |
| Ethyl alcohol | 20 | 10 |
| Pluronic F-108* | 8 | 4 |
| Flavor | 0.4 | 0.2 |
| Glycerin | 20 | 10 |
| Saccharin | 0.06 | 0.03 |
| 0.1% FD & C Color | 0.6 | 0.3 |
| Deionized water q.s. | 100.0 | |

*A polyalkene oxide block polymer

Solution B (Zinc-Polymer Complex)

A 2% polymer solution is prepared by adding methyl vinyl ethermaleic anhydride copolymer (Gantrez) to 500 ml of water (pre-heated to 90° C.) with continuous stirring until a clear solution is obtained. The polymer solution is cooled to room temperature and the pH is adjusted to 5.5 with addition of 3N ammonium hydroxide. Then 0.05 M of zinc oxide salt is added with stirring. The mixture is a clear solution.

500 ml of solution A is added to 500 ml of solution B with continuous stirring (e.g. magnetic stirrer). The pH of the mixture is between 4 and 6, and is a clear mouth rinse. The final concentration of zinc salt in the mouthrinse is 0.025M and of polymer is 1%.

Equilibrium dialysis studies showed that the zinc-polymer complex in a typical mouth rinse formulation retains its identity in the presence of saliva salts and exhibits a slow rate of dissociation. After 10 minutes, 3% dissociation was noted; after 1 hour, 5% dissociation occured; and after 24 hours, 12% dissociation was measured. The slow release of the zinc ions and the increased retention of the zinc in the oral cavity enhance the effectiveness of instant oral compositions containing the zinc-polymer complex against mouth odor, plaque, gingivitis and other oral disorders.

EXAMPLE 5

| Mouthwash | |
|---|---|
| | % |
| Ethyl alcohol | 15.0 |
| Non-ionic detergent (Pluronic F-108)[1] | 4.0 |
| Flavor | 0.2 |
| Glycerin | 10.0 |
| Saccharin | 0.03 |
| FD & C color (0.1) | 0.3 |
| Anionic polymer (Gantrez 119)[2] | 1.0 |
| Zinc chloride | 0.025 |
| Water q.s. | 100ml. |

[1] A polyalkene oxide block polymer
[2] Copolymer of maleic anhydride and methyvinyl ether having a malecular weight of 250,000.

The zinc chloride powder is added to a 2% aqueous solution of the anionic polymer and stirred until dissolved and the pH is adjusted to 5.5 with ammonium hydroxide and then the mouth rinse concentrate containing the remaining ingredients is added to the zinc-polymer solution in accordance with the procedure of Example 3.

In vitro VSC Inhibition tests on this mouthrinse in the presence of saliva gave the following results:

Table III

| | % VSC Inhibition | |
|---|---|---|
| Sample | 3 hrs incubation | 24 hrs incubation |
| zinc chloride mouthrinse | 72 | 50 |
| zinc chloride-polymer rinse | 72 | 80 |

These results clearly show the long range effectiveness of the zinc-polymer complex as a mouth odor inhibitor.

EXAMPLE 6

| Dental Cream | |
|---|---|
| | % |
| Anionic polymer of Example 1 | 1.0 |
| Zinc chloride | 0.025 |
| Nonionic detergent* | 1.00 |
| Glycerine | 22.00 |
| Sodium pyrophosphate | 0.25 |
| Carboxymethyl cellulose | 0.85 |
| Sodium saccharin | 0.20 |
| Sodium benzoate | 0.50 |
| Calcium carbonate (precipitated) | 5.00 |
| Dicalcium phosphate dihydrate | 46.75 |
| Flavor | 0.80 |

| -continued | |
|---|---|
| Dental Cream | |
| | % |
| Water q.s. | |

*Tween 80-Polyoxyethlene (20 moles ethylene oxide) sorbitan monooleate.

The zinc-polymer complex is prepared in accordance with the procedure of Example 4. The remaining ingredients are admixed with agitation to form a base paste, which is then mixed with the zinc-polymer complex, using either equal volumes or weights of the base paste and the preformed zinc-polymer complex.

An effective amount, e.g., about 0.01–5% zinc compound and 0.1 to 10% anionic polymer may also be incorporated in an inert carrier or dissolved in a suitable vehicle in the formulation of chewing gums and lozenges. Similarly, the zinc-polymer complex may also be incorporated into a mouth spray. A typical lozenge formula contains the following ingredients, in percent by weight, based on the weight of the total formulation:

| 75% | to | 98% | Sugar |
|---|---|---|---|
| 1% | to | 20% | Corn Syrup |
| .1% | to | 1% | Flavor oil |
| 0% | to | .03% | Colorant(s) |
| .1% | to | 5% | Tableting Lubricant |
| .2% | to | 2% | Water |
| .1% | to | 10% | Anionic polymer |
| .01% | to | 5% | Zn compound |

Sugarless pressed candy may also be formulated to include the complex of this invention. For products of this type, which usually contain powdered sorbitol instead of sugar, synthetic sweeteners are mixed with the powdered sorbitol and flavor(s), colorant(s) and a tablet lubricant are then added. The formula is introduced into a tablet machine to shape the final product. A typical sugarless pressed candy contains the following ingredients, in percent by weight, based on the weight of the total formulation:

| 98% | to | 99.5% | Sorbitol |
|---|---|---|---|
| .1% | to | .9% | Flavor(s) |
| 0% | to | .02% | Synthetic Sweeteners |
| 0% | to | .03% | Colorant(s) |
| .05% | to | 1% | Tableting Lubricant |

Obviously many variations of the above described procedures may be used to prepare pressed candies.

A typical chewing gum may contain the following ingredients, in percent by weight based on the weight of the total gum formulation:

| Ingredients | Weight Percent |
|---|---|
| Gum Base | From about 10% to about 40% |
| Sucrose | From about 50% to about 75% |
| Corn Syrup or Glucose | From about 10% to about 20% |
| Flavor Material | From about 0.4% to about 5% |
| Anionic polymer | From about .1% to about 10% |
| Zn compound | From about .01% to about 5% |

An alternate chewing gum formulation is as follows:

| Ingredients | Weight Percent |
|---|---|
| Gum Base | From about 10% to about 50% |
| Binder | From about 3% to about 10% |
| Filler (Sorbitol, Mannitol or combinations thereof) | From about 5% to about 80% |

-continued

| Ingredients | Weight Percent |
| --- | --- |
| Artificial Sweetener and Flavor | From about 0.1% to about 5% |
| Anionic Polymer | From about .1% to about 10% |
| Zn compound | From about .01% to about 5% |

In certain sugarless gums, there is used as the binder ingredient a solution of sorbitol in water containing from about 10% to about 80%, preferably from about 50% to about 75% by weight of sorbitol in $H_2O$. In others, there is used a gum acacia-in-water system containing from about 30% to about 60%, preferably from about 45% to about 50% by weight of gum acacia powder.

The above chewing gum formulations are exemplary only. Many additional formulations are described in the prior art, and in carrying out this invention, such formulations can be employed. It is also possible to prepare an acceptable chewing gum product containing a gum base, flavoring material and Zn-polymer complex according to the teaching of this invention.

The ingredient referred to heretofore in the formulations simply as "gum base" is susceptible to many variations. In general, a gum base is prepared by heating and blending various ingredients, such as natural gums, synthetic resins, waxes, plasticizers, etc. in a manner well known in the art. Typical examples of the ingredients found in a chewing gum base are masticatory substances of vegetable origin, such as chicle, crown gum, nispero, rosidinha, jelutong, pendare, perillo, niger gutta, tunu, etc.; masticatory substances of synthetic origin such as butadiene-styrene polymer, isobutylene-isoprene copolymer, paraffin, petroleum wax, polyethylene, polyisobutylene, polyvinylacetate, etc.; plasticizers such as lanolin, stearic acid, sodium stearate, potassium stearate, etc.

A preferred ingredient of instant composition is a non-ionic organic surfactant which provides increased prophylactic action, assists in achieving thorough and complete dispersion of instant compositions throughout the oral cavity and renders instant compositions more cosmetically acceptable. The non-ionic surfactant imparts to the composition detersive and foaming properties, as well as maintains the flavoring materials in solution (i.e., solubilizes flavor oils). In addition, the non-ionics are completely compatible with the zinc-anionic complex of this invention, thereby providing for a stable, homogeneous composition of superior mouth odor control.

The non-ionic organic surface active compounds which are contemplated are commercially known and comprise water-soluble products which are derived from the condensation of an alkylene oxide or equivalent reactant and a reactive-hydrogen hydrophobe. The hydrophobic organic compounds may be aliphatic, aromatic or heterocyclic, although the first two classes are preferred. The preferred types of hydrophobes are higher aliphatic alcohols and alkyl phenols, although others may be used such as carboxylic acids, carboxamides, sulphonamides, etc. The ethylene oxide condensates with higher-alkyl phenols represent a preferred class of non-ionic compounds. Usually the hydrophobic moiety should contain at least about 6 carbon atoms, and preferably at least about 8 carbon atoms, and may contain as many as about 50 carbon atoms or more. The amount of alkylene oxide will vary considerably, depending upon the hydrophobe, but as a general guide and rule, at least about 5 moles of alkylene oxide per mole of hydrophobe should be used. The upper limit of alkylene oxide will vary also, but no particular criticality can be ascribed thereto. As much as 200 or more moles of alkylene oxide per mole of hydrophobe may be employed. While ethylene oxide is the preferred and predominating oxyalkylating reagent, other lower alkylene oxides such as propylene oxide, butylene oxide, and the like, may also be used or substituted in part for the ethylene oxide. Other non-ionic compounds which are suitable are the polyoxyalkylene esters of the organic acids such as the higher fatty acids, the rosin acids, tall oil acids, acids from petroleum oxidation products, etc. These esters will usually contain from about 10 to about 22 carbon atoms in the acid moiety and from about 12 to about 30 moles of ethylene oxide or its equivalent.

Still other non-ionic surfactants are the alkylene oxide condensates with the higher fatty acid amides. The fatty acid group will generally contain from about 8 to about 22 carbon atoms and this will be condensed with about 10 to about 50 moles of ethylene oxide as the preferred illustration. The corresponding carboxamides and sulphonamides may also be used as substantial equivalents.

Still another class of non-ionic products are the oxyalkylated higher aliphatic alcohols. The fatty alcohols should contain at least 6 carbon atoms, and preferably at least about 8 carbon atoms. The most preferred alcohols are lauryl, myristyl, cetyl, stearyl and oleyl alcohols and the acid alcohols should be condensed with at least about 6 moles of ethylene oxide, and preferably about 10 to 30 moles of ethylene oxide. A typical non-ionic product is oleyl alcohol condensed with 15 moles of ethylene oxide.

The amount of non-ionic may generally be varied from about 0.2–3.0% by weight of the total formulation, depending on the specific nature of the non-ionic utilized, as well as on the amounts and nature of the other ingredients in the oral formulation.

Although this invention has been described with reference to specific examples, it will be apparent to one skilled in the art that various modifications may be made thereto which fall within its scope.

What is claimed is:

1. A non-astringent tasting oral composition to control mouth odor containing as the essential agent, a zinc-polymer complex having a pH of about 4.5 to 6, wherein said polymer is anionic, linear and contains ionizable carboxyl, sulfonic or phosphonic groups selected from the group consisting of
    1. a copolymer of maleic anhydride with ethylene, or styrene, or isobutylene, or polymethyl vinyl ether, or polyethylvinyl ether, having recurring groups:

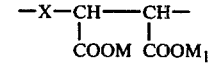

wherein M and $M_1$ are individually hydrogen, sodium, potassium or ammonium and may be the same or different, and X is ethylene, styrene, isobutylene, methylvinyl ether, and ethylvinyl ether,
    2. a polyacrylic acid and polyacrylates thereof having recurring groups:

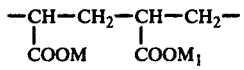

wherein M and $M_1$ have the same meaning as above,
3. a polyitaconic acid and polyitaconates thereof having recurring groups:

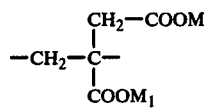

wherein M and $M_1$ have the same meaning as above,
4. a polyolefin sulfonate having recurring groups:

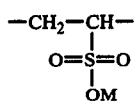

wherein M has the same meaning as above,
5. a polyvinyl phosphonate having recurring groups:

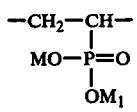

wherein M and $M_1$ have the same meaning as above,
6. and a polyvinyl phosphate having recurring groups:

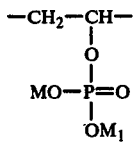

wherein M and $M_1$ have the same meaning as above, and is ionically bound to a physiologically acceptable zinc salt selected from the group consisting of

| | |
|---|---|
| zinc acetate | zinc isovalerate |
| zinc acetylacetonate | zinc D-lactate |
| zinc ammonium sulfate | zinc DL-lactate |
| zinc benzoate | zinc laurate |
| zinc bromide | zinc hexafluorosilicate |
| zinc beryllium orthosilicate | zinc methacrylate |
| zinc borate | zinc molybdate |
| zinc butylphthalate | zinc naphthenate |
| zinc butylxanthate | zinc octoate |
| zinc caprylate | zinc oleate |
| zinc carbonate | zinc orthophosphate |
| zinc chloroanilate | zinc phenolsulfonate |
| zinc chlorate | zinc pyridine-2-thiol-1-oxide |
| zinc chromate | zinc pyrophosphate |
| zinc citrate | zinc resinate |
| zinc cyclohexanebutyrate | zinc salicylate |
| zinc chloride | zinc sulfate |
| zinc gallate | zinc nitrate |
| zinc fluoride | zinc selenide |
| zinc alpha-glucoheptonate | zinc stearate |
| zinc gluconate | zinc sulfanilate |
| zinc glycerophosphate | zinc tartrate |
| zinc hydroxide | zinc tellurate |
| zinc 8-hydroxyquinoline | zinc tungstate |
| zinc 12-hydroxystearate | zinc valerate |
| zinc iodide | zinc vanadate |
| zinc acrylate | zinc tribromosalicylanilide |
| zinc oxide | zinc ricinoleate |
| zinc propionate, | | the ratio of zinc salt to anionic polymer being within the range of about 2:1 to 1:4.

2. A composition in accordance with claim 1, wherein the zinc compound constitutes about 0.01 to 5%, and the anionic polymer constitutes about 0.1 to 10% by weight of the composition.

3. A composition in accordance with claim 1, wherein said anionic polymer is a copolymer of maleic anhydride and methylvinyl ether.

4. A composition in accordance with claim 1, wherein said zinc salt is zinc oxide.

5. A composition in accordance with claim 1, wherein said zinc compound is zinc chloride.

6. A composition in accordance with claim 1, wherein said zinc salt is zinc propionate.

7. A method of preventing and controlling mouth odor which comprises applying the composition of claim 1 to the oral cavity, wherein the zinc-anionic polymer complex adsorbs onto the oral surfaces forming a reservoir of zinc ions which is slowly released within said cavity.

8. A method in accordance with claim 7 which comprises washing the oral cavity with an aqueous mouthrinse.

9. A method in accordance with claim 7 which comprises brushing the teeth with a dental cream.

10. A composition in accordance with claim 1, wherein the anionic polymer is selected from the group consisting of copolymers of an unsaturated polybasic carboxylic acid or anhydride and of an olefin having 2 or more carbon atoms per molecule; polyolefin sulfonates; polyolefin phosphonates; and polyolefin phosphates wherein the olefin group contains 2 or more carbon atoms.

* * * * *